US010168275B2

(12) United States Patent
Orcutt (10) Patent No.: US 10,168,275 B2
(45) Date of Patent: Jan. 1, 2019

(54) UNTUNED RESONANCE TRACED GAS SENSING (71) Applicant: INTERNATIONAL BUSINESS MACHINES CORPORATION, Armonk, NY (US)

(72) Inventor: Jason S. Orcutt, Katonah, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/603,084

(22) Filed: May 23, 2017

(65) Prior Publication Data
US 2018/0340883 A1 Nov. 29, 2018

(51) Int. Cl.
G01N 21/25 (2006.01)
G01N 21/27 (2006.01)
G01N 33/00 (2006.01)
G01N 21/31 (2006.01)
G02B 6/293 (2006.01)

(52) U.S. Cl.
CPC ......... G01N 21/255 (2013.01); G01N 21/27 (2013.01); G01N 21/31 (2013.01); G01N 33/0022 (2013.01); G01N 33/0047 (2013.01); G02B 6/29338 (2013.01); G01N 2201/0873 (2013.01)

(58) Field of Classification Search
CPC ........ G01N 21/25; G01N 21/27; G01N 21/31; G01N 33/0022; G01N 33/0047; G02B 6/293; G01J 3/02; G01J 3/51
See application file for complete search history.

(56) References Cited

U.S. PATENT DOCUMENTS

| 6,504,145 | B1 | 1/2003 | Romanini et al. |
| 7,504,263 | B2 | 3/2009 | Lehmann et al. |
| 8,063,373 | B2 | 11/2011 | Miller |
| 8,567,232 | B2 | 10/2013 | Ackley |
| 9,476,770 | B1 * | 10/2016 | Green ................ G01J 3/42 |
| 2009/0249861 | A1 | 10/2009 | Van Dijk et al. |
| 2015/0276590 | A1 | 10/2015 | Koulikov et al. |

FOREIGN PATENT DOCUMENTS

CN 103398964 11/2013

OTHER PUBLICATIONS

Arslanov, et al., "Rapid and Sensitive Trace Gas Detection with Continuous Wave Optical Parametric Oscillator-based Wavelength Modulation Spectroscopy", Appl Phys B, Sep. 2010, pp. 223-228.

* cited by examiner

Primary Examiner — Abdullahi Nur
(74) Attorney, Agent, or Firm — Tutunjian & Bitetto, P.C.; Vazken Alexanian (57) ABSTRACT Methods and systems for detecting a gas or liquid in an environment include measuring a reference signal at each of a set of wavelengths by passing a signal at each wavelength through a reference cell having a gas or liquid to be detected. A sensing signal is measured at each of the plurality of wavelengths by coupling each wavelength to a ring resonator in the environment. A set of wavelengths that correspond to an absorption curve of the gas or liquid to be detected is determined. A concentration of the gas or liquid to be detected in the environment is determined based on amplitudes of the sensing signal at each of the set of wavelengths.

20 Claims, 4 Drawing Sheets

UNTUNED RESONANCE TRACED GAS SENSING

STATEMENT REGARDING FEDERALLY SPONSORED RESEARCH OR DEVELOPMENT

This invention was made with Government support under Contract No.: DE-AR0000540 awarded by Department of Energy. The Government has certain rights in this invention.

BACKGROUND

Technical Field

The present invention generally relates to gas sensing and, more particularly, methods and structures for gas sensing that use optical resonance yet do not need to be tuned.

Description of the Related Art

Existing gas sensors based on optical signals in waveguides need extremely long transmission paths to be made practical. However, long transmission paths correspond to large instruments, which can make it difficult to deploy such sensors in the field.

SUMMARY

A method for detecting a gas or liquid in an environment includes measuring a reference signal at each of a set of wavelengths by passing a signal at each wavelength through a reference cell having a gas or liquid to be detected. A sensing signal is measured at each of the plurality of wavelengths by coupling each wavelength to a ring resonator in the environment. A set of wavelengths that correspond to an absorption curve of the gas or liquid to be detected is determined. A concentration of the gas or liquid to be detected in the environment is determined based on amplitudes of the sensing signal at each of the set of wavelengths.

A system for detecting a gas or liquid in an environment includes a reference cell having a gas or liquid to be detected. A ring resonator is exposed to the environment. A first detector is configured to measure a reference signal at each of a plurality of wavelengths output by the reference cell. A second detector is configured to measure a sensing signal at each of the plurality of wavelengths after each wavelength is coupled to the ring resonator. A detection module is configured to determine a set of wavelengths that correspond to an absorption curve of the gas or liquid to be detected and to determine a concentration of the gas or liquid to be detected in the environment based on amplitudes of the sensing signal at each of the set of wavelengths.

A system for detecting a methane in an environment includes a reference cell having a known concentration of methane gas. A ring resonator is exposed to the environment. A first detector is configured to measure a sensing signal at each of a plurality of wavelengths after each wavelength is coupled to the ring resonator, each said plurality of wavelengths being resonant in the ring resonator. A second detector configured to measure a reference signal at each of the plurality of wavelengths output by the reference cell. A detection module is configured to determine a set of wavelengths that correspond to an absorption curve of methane gas and to determine a concentration of methane in the environment based on amplitudes of the sensing signal at each of the set of wavelengths.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention provide sensitive gas sensing using low-loss waveguide sensors that have relatively short transmission paths. An optical resonator ring is used as the sensing element, with a path length less than a tenth of what would be needed to provide a similar sensitivity with a linear waveguide.

Figure 1:
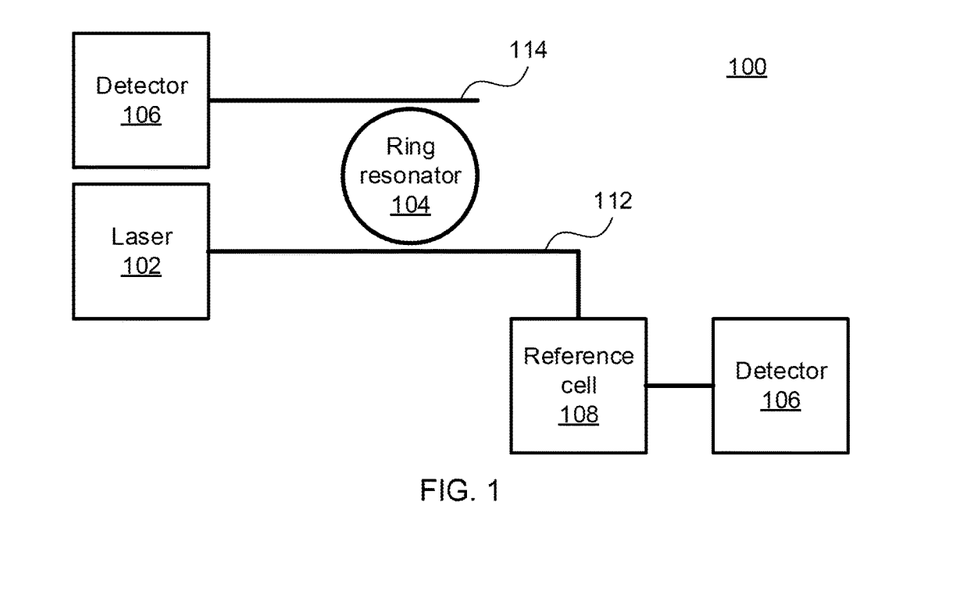
FIG. 1 is a block diagram of an untuned resonance sensing apparatus in accordance with an embodiment of the present invention.

Referring now to FIG. 1, a block diagram of the sensing apparatus 100 is shown. A laser 102 generates an optical signal and launches the optical signal on an input waveguide 112. It is specifically contemplated that the waveguide 112 may be formed from a low-loss material, characterized by small, but non-zero, amounts of power being lost as the signal propagates. The waveguide 112 may be formed from silicon nitride waveguides fabricated on top of a silicon dioxide lower cladding. The role of the top cladding is filled by the gas in either the sensing region 104 or reference cell region 108. To increase the electric field overlap with the gas, a silicon nitride waveguide may optionally be undercut, such that the silicon dioxide is etched with an etchant that is chemically selective to the silicon nitride waveguide. The entire system may be fabricated on top of a silicon wafer. In cross-section, a 200 nm thick silicon nitride waveguide may be patterned to a 2000 nm width on top of a 4000 nm silicon dioxide layer on a silicon wafer. It is specifically contemplated that the low-loss material will have propagation losses below about 1 dB/cm, with a loss-per-meter of about 0.1 dB/cm being specifically contemplated.

The input waveguide 112 passes by sensing ring resonator 104 before passing through reference cell 108 and reaching detector 106. It is contemplated that the detector 106 may be any appropriate detection mechanism, including without limitation semiconductor-based photodetectors. The reference cell 108 includes a sample of the material that the detector is designed for. In one specific embodiment, the reference cell may include a sample of methane gas at a known density. The path of the input waveguide 112 through the reference cell may be serpentine or, in the presence of a high reference material concentration, a relatively short straight path.

The sensing ring resonator 104 is exposed to the environment being analyzed. The sensing ring 104 is itself formed from a low-loss waveguide in a ring configuration and is coupled to the input waveguide 112 with a predetermined coupling coefficient. In one specific embodiment, the coupling coefficient between the sensing ring 104 and the input waveguide 112 may be e.g., 25%, such that 25% of the power traveling through the input waveguide is transmitted to the sensing ring 104. The coupling between the input waveguide 112 and the sensing ring 104 may be accomplished by a distinct coupling device or, in the embodiments described in detail herein, through evanescent-wave coupling, whereby power is transmitted from one medium to a nearby medium (e.g., from the input waveguide 112 to the sensing ring 104) without an physical connection between the two media.

The sensing ring 104 promotes whispering gallery resonant modes at periodic wavelengths based on the dimensions of the waveguide ring. Whispering gallery resonance is a property of circular transmission media whereby waves traveling in the sensing ring 104 constructively and destructively interfere at points, creating a stable resonance of standing waves within the ring. Whispering gallery resonances are related to the radius r of a ring resonator as $m\lambda_m = 2\pi r n_{eff}$, where m is an integer representing the mode number, $\lambda_m$ is a resonant wavelength at mode m, and $n_{eff}$ is the effective index of refraction of the waveguide material.

Thus, to resonate, the circumference of the sensing ring 104 needs to be an integer multiple of the wavelength of the transmitted light. In one specific embodiment, the circumference of the sensing ring 104 may be about 5 cm. In alternative embodiments, the sensing ring may follow a closed serpentine path for a more compact footprint than a circular ring. In either case, the bend radius is sufficiently large to eliminate radiation and interface losses. The bend radius may be, for example, about 0.5 mm in the example of a silicon nitride platform.

The sensing ring 104 couples to the output waveguide 114. This coupling may also be performed by evanescent-wave coupling or by any other appropriate coupling mechanism. The coupling coefficient between the sensing ring 104 and the output waveguide 114 may, again, be about 25%. The output waveguide 114 leads to a detector 106 which again may be a photodetector or any other appropriate detecting mechanism.

The sensing ring 104 and the portion of the input waveguide 112 in the reference cell 108 are both exposed to environments of interest over known path lengths. As the optical signal passes through the waveguides in these areas, the signal couples to the surrounding media, resulting in power loss. By measuring the power loss of the signal at the output waveguide 114 compared to the power loss of the signal that passes through the reference cell 108, the sensing system 100 provides information as to whether the gas present in the reference cell 108 is also present at the sensing ring 104.

Following the example of methane detection, methane has a linewidth between 4 GHz and 5 GHz, depending on atmospheric pressure. Thus, methane will absorb signals at a wide range of frequencies around its peak absorption frequency. In such a case, precise tuning of the input frequency to the resonant frequency of the gas in question is not needed—an average of about 3 measurements anywhere within the full width at half maximum of the gas's absorption curve around the resonant frequency is sufficient to detect the gas. Thus, in the specific embodiment of detecting methane, a specific exemplary embodiment of the sensing ring resonator 104 would have a free spectral range of about 1.7 GHz for a 10 cm circumference nitride ring path length for a group index of 1.81. This ensures that there will be sufficient overlap between the sensing ring's transmission resonances and the methane absorption curve to perform the measurement. Alternative embodiments for the detection of methane may include a sensing ring resonator 104 that has a free spectral ranges in the range between about 10 MHz and about 2 GHz in the case of methane at 1650.96 nm optical wavelength. While methane and a nitride waveguide architecture are specifically contemplated herein, it should be understood that other gases may be detected and that other waveguide materials may be used to achieve a similar effect.

In the specific embodiment described above, having a sensing ring resonator 104 with a circumference of about 5 cm, where the waveguide path loss is about 0.1 dB/cm and the coupling coefficients between the sensing ring 104 and the input waveguide 112 and the output waveguide 114 are about 25%, a particular methane concentration may increase the waveguide loss drop by 0.01 dB/cm, resulting in a change in signal power at the output waveguide 114 of about 0.8 dB. This is equivalent to the loss that would be produced by an 80 cm straight path measurement, providing an increase in sensitivity per centimeter of waveguide path length of over 10×. If the detectors' sensitivity is about 0.0001 dB, then the sensing system 100 would have a methane sensitivity of about 10 ppm (assuming 25% effective overlap integral with gas). In this case, the effective overlap is the ratio of the equivalent absorption path length of the gas in free space to the actual absorption path length from to the gas in the waveguide due to modal electric field overlap with the gas region.

The light that is not coupled through the sensing ring 104 to the ambient gas of interest continues on waveguide 112 to an enclosed gas cell 108. In the enclosed gas cell 108, a high concentration of the target gas species can be sealed over the waveguide and a non-resonant waveguide path may be used to detect the absorption lines of the gas for sensor calibration.

Figure 2:
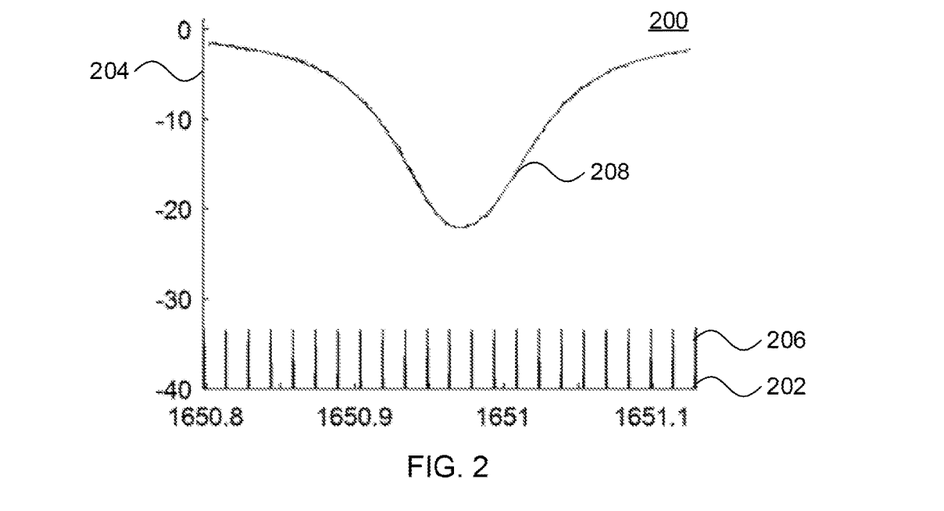
FIG. 2 is a graph illustrating a relationship between resonances of a ring resonator and the methane gas absorption curve in accordance with an embodiment of the present invention.

Referring now to FIG. 2, an exemplary graph 200 is shown with resonances of the sensing ring 104 and the absorption curve for methane overlaid. The horizontal axis shows wavelength, measured in nanometers, while the vertical axis provides transmission power in decibels. Periodic spikes 206 are shown that represent the resonances of a given sensing ring 104. The methane absorption curve 208 is superimposed to show that multiple spikes 206 are present within the curve's full width at half magnitude. By measuring the amplitudes of the output at detector 106 at these wavelengths, comparing the amplitudes to the amplitude measured after passage through the reference cell 108, it can be determined whether methane is present around the ring resonator 104 and at what concentration.

Using the sensor calibration provided by the reference cell transmission path, the relative methane absorption strength associated with the frequency of each transmission resonance can be calculated. With this information, the measured transmission magnitude and full width at half magnitude for one or more sensor resonances (in particular, the resonances having the largest relative methane absorption strengths as compared to sensor resonances having the lowest relative methane absorption strengths) can then be used to calculate the methane concentration in the gas exposed to the sensing ring resonator 104.

The expected effective absorption coefficient is denoted herein as $\alpha_{eff}$. This quantity is used in the linear regime of weak absorption and is measured in, e.g., units of inverse centimeters at concentrations on the order of 1 ppm in the case of methane. Measured transmission functions for the sensor resonances overlapping with the gas's absorption line can be fit to calculate the effective total sensor propagation loss in inverse centimeters for two resonances: $\alpha_{gas}$ and $\alpha_{air}$, with the former representing the absorption coefficient for the gas being detected and the latter representing the absorption coefficient for air. This fit of propagation loss can be accomplished using, e.g., a transmission matrix analysis of the ring resonator 102 or well-known analytical equations.

The calculation of the concentration of the gas to be detected in the environment of the sensor 104 then only needs knowledge of the effective modal electric field overlap with the gas for the sensor waveguide. The overlap is represented as a unitless confinement factor $\Gamma_{gas}$ and can be taken as an a priori calibration parameter known from the fabrication process or can be calculated from transmission measurement in the reference cell 108. Calculation of the confinement factor may be accomplished by taking the ratio of the measured propagation loss as compared to the expected gas absorption for the known reference cell concentration. The gas concentration can then be calculated in this example as:

$$C_{gas} = \frac{(\alpha_{gas} - \alpha_{air})}{\Gamma_{gas}\alpha_{eff}}$$

The calculations for detecting a liquid instead of a gas follow a similar form.

Figure 3:
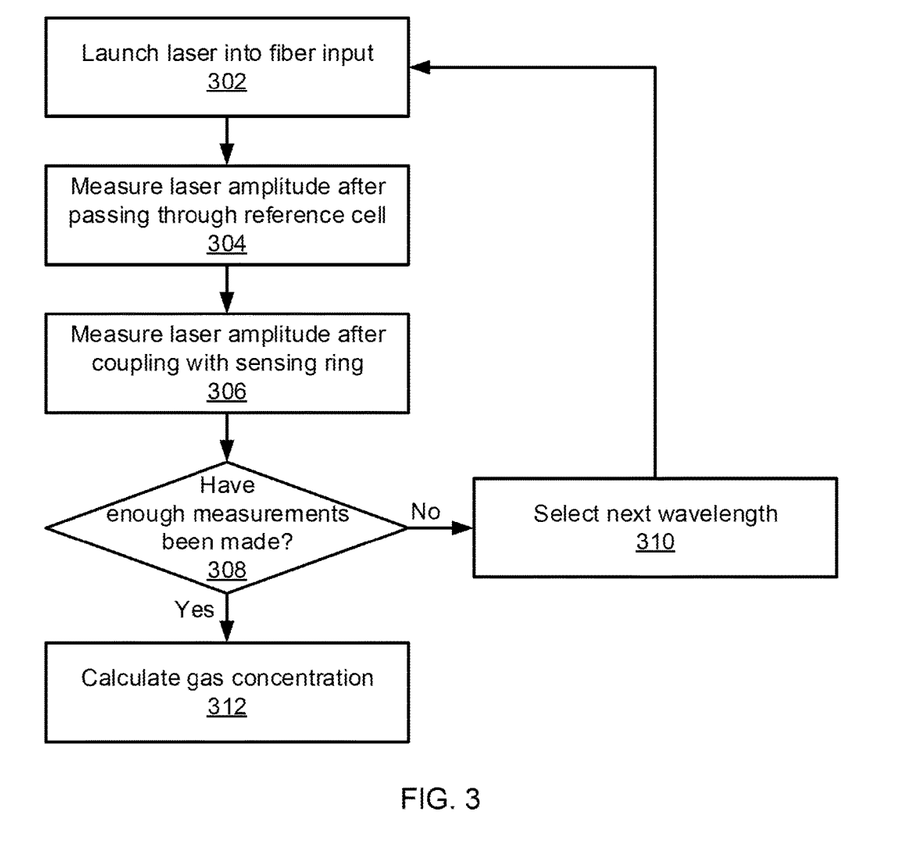
FIG. 3 is a block/flow diagram of a method of concentration sensing in accordance with an embodiment of the present invention.

Referring now to FIG. 3, a method of gas detection is shown. Block 302 launches light into the fiber 112 at a first wavelength from laser 102. It should be understood that this first wavelength need not be precisely tuned to the absorption spectrum of the gas to be detected—in one example, the lowest frequency the laser 102 is capable of producing may be used.

Block 304 then measures the laser amplitude using a detector 106 after the waveguide 112 has passed through reference cell 108. Block 306 measures the laser amplitude using a detector after the light has coupled to the sensing ring 104 and then to output waveguide 114. These two signals are stored with the corresponding wavelength.

Block 308 determines whether sufficient measurements have been made. In one embodiment, block 308 may determine whether an upper range of possible emissions from the laser 102 has been reached. In another embodiment, the measurements may be considered to determine whether a characteristic signal for the gas to be detected has been recognized. Any appropriate mechanism for making the determination of block 308 may be used. If more measurements are needed, block 310 selects the next wavelength and block 302 launches the new wavelength into the fiber 112. The next wavelength may be a next resonance of the sensing ring 104 or may, alternatively, simply be an incremental change in the wavelength determined by the control mechanism of the laser 102.

Block 312 then calculates the gas concentration at the sensing ring 104. This may be accomplished by first determining which wavelengths correspond to detection of the gas in question (e.g., by looking for amplitude changes in measured signals that have passed through the reference cell 108). The measurements from the sensing ring 104 at the determined wavelengths are then compared to a baseline amplitude to determine a degree of amplitude change. Based on this degree of amplitude change, block 312 determines whether the gas is present, and at what concentration.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 4:
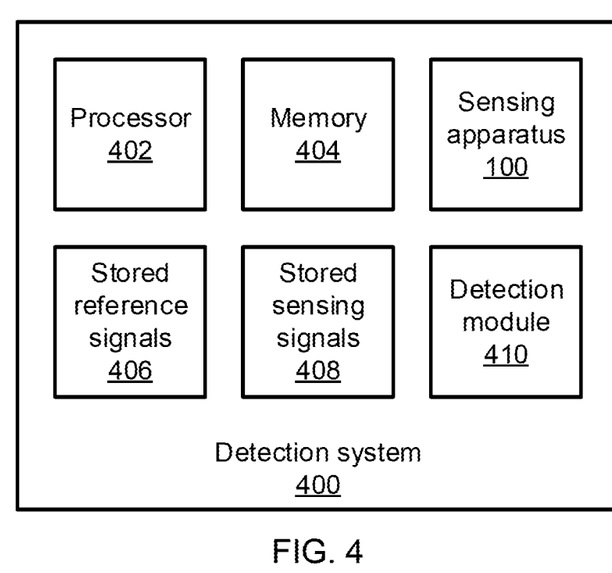
FIG. 4 is block diagram of a detection system in accordance with an embodiment of the present invention.

Referring now to FIG. 4, a system 400 for detecting the presence of, e.g., a gas or liquid is shown. The system 400 includes a hardware processor 402 and memory 404. The system 400 also includes a sensing apparatus 100 which includes the sensing ring 104 that is exposed to the environment in question. The sensing apparatus 100 makes measurements at various wavelengths and stores the corresponding reference signals 406 and sensing signals 408 in the memory 404. The system 400 further includes one or more functional modules that may be implemented as software in some embodiments that is stored in memory and executed by hardware processor 402. In other embodiments, the functional module(s) may be implemented as one or more discrete hardware components in the form of, e.g., application specific integrated chips or field programmable gate arrays.

In particular, detection module 410 uses the stored reference signals 406 to determine particular stored sensing signals 408 that correspond to wavelengths within the absorption spectrum of the gas or liquid to be detected. Detection module 410 then analyzes the amplitudes of the stored sensing signals 408 that correspond to the gas or liquid and determines a concentration of that gas or liquid in the environment.

Figure 5:
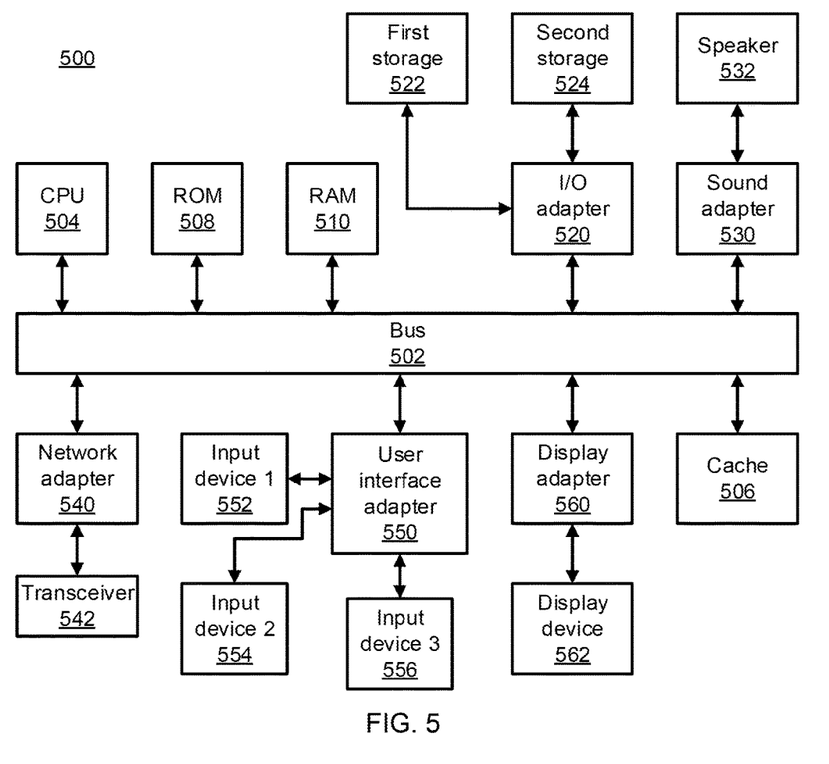
FIG. 5 is a block diagram of a processing system in accordance with an embodiment of the present invention.

Referring now to FIG. 5, an exemplary processing system 500 is shown which may represent the hardware of the detection system 400. The processing system 500 includes at least one processor (CPU) 504 operatively coupled to other components via a system bus 502. A cache 506, a Read Only Memory (ROM) 508, a Random Access Memory (RAM) 510, an input/output (I/O) adapter 520, a sound adapter 530, a network adapter 540, a user interface adapter 550, and a display adapter 560, are operatively coupled to the system bus 502.

A first storage device 522 and a second storage device 524 are operatively coupled to system bus 502 by the I/O adapter 520. The storage devices 522 and 524 can be any of a disk storage device (e.g., a magnetic or optical disk storage device), a solid state magnetic device, and so forth. The storage devices 522 and 524 can be the same type of storage device or different types of storage devices.

A speaker 532 is operatively coupled to system bus 502 by the sound adapter 530. A transceiver 542 is operatively coupled to system bus 502 by network adapter 540. A display device 562 is operatively coupled to system bus 502 by display adapter 560.

A first user input device 552, a second user input device 554, and a third user input device 556 are operatively coupled to system bus 502 by user interface adapter 550. The user input devices 552, 554, and 556 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 552, 554, and 556 can be the same type of user input device or different types of user input devices. The user input devices 552, 554, and 556 are used to input and output information to and from system 500.

Of course, the processing system 500 may also include other elements (not shown), as readily contemplated by one of skill in the art, as well as omit certain elements. For example, various other input devices and/or output devices can be included in processing system 500, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 500 are readily contemplated by one of ordinary skill in the art given the teachings of the present principles provided herein.

Having described preferred embodiments of untuned resonance traced gas sensing (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method of detecting a gas or liquid in an environment, comprising:
   measuring a reference signal at each of a plurality of wavelengths by passing a signal at each wavelength through a reference cell having a gas or liquid to be detected;
   measuring a sensing signal at each of the plurality of wavelengths by coupling each wavelength to a ring resonator in the environment;
   determining a set of wavelengths that correspond to an absorption curve of the gas or liquid to be detected; and
   determining a concentration of the gas or liquid to be detected in the environment by comparing amplitudes of the sensing signals at each of the set of wavelengths that correspond to the absorption curve to reference signals measured at each of the set of wavelengths.

2. The method of claim 1, wherein determining the set of wavelengths comprises determining wavelengths that fall within a full width at half maximum of the absorption curve.

3. The method of claim 2, wherein determining the set of wavelengths further comprises determining the full width at half maximum based on the detected reference signals.

4. The method of claim 1, wherein the set of wavelengths consists of wavelengths that are resonant in the ring resonator.

5. The method of claim 1, wherein the gas or liquid to be detected is methane gas.

6. The method of claim 5, wherein the ring resonator has a circumference of about 5 cm.

7. The method of claim 1, wherein the ring resonator is a silicon nitride waveguide on a silicon dioxide lower cladding.

8. The method of claim 1, further comprising launching a laser onto an input waveguide at each of the plurality of wavelengths.

9. The method of claim 8, wherein measuring the reference signal comprises measuring an output of the input waveguide and wherein measuring the sensing signal comprises measuring an output of an output waveguide that couples to the sensing ring.

10. The method of claim 1, wherein determining the concentration comprises calculating the concentration C of the liquid or gas to be detected as:

$$C = \frac{(\alpha_{det} - \alpha_{air})}{\Gamma_{det}\alpha_{eff}}$$

where $\alpha_{det}$ is the absorption coefficient of the liquid or gas to be detected, $\alpha_{air}$ is the absorption coefficient of air, $\Gamma_{det}$ is a confinement factor for the liquid or gas to be detected, and $\alpha_{eff}$ is the expected absorption coefficient.

11. A system for detecting a gas or liquid in an environment, comprising:
   a reference cell having a gas or liquid to be detected;
   a ring resonator exposed to the environment;
   a first detector configured to measure a reference signal at each of a plurality of wavelengths output by the reference cell;
   a second detector configured to measure a sensing signal at each of the plurality of wavelengths after each wavelength is coupled to the ring resonator; and
   a detection module configured to determine a set of wavelengths that correspond to an absorption curve of the gas or liquid to be detected and to determine a concentration of the gas or liquid to be detected in the environment by comparing amplitudes of the sensing signals at each of the set of wavelengths that correspond to the absorption curve to reference signals measured at each of the set of wavelengths.

12. The system of claim 11, wherein the detection module is further configured to determine wavelengths that fall within a full width at half maximum of the absorption curve.

13. The system of claim 12, wherein the detection module is further configured to determine the full width at half maximum based on the detected reference signals.

14. The system of claim 11, wherein the set of wavelengths consists of wavelengths that are resonant in the ring resonator.

15. The system of claim 11, wherein the gas or liquid to be detected is methane gas.

16. The system of claim 15, wherein the ring resonator has a circumference of about 5 cm.

17. The system of claim 11, wherein the ring resonator is a silicon nitride waveguide on a silicon dioxide lower cladding.

18. The system of claim 11, further comprising launching a laser configured to launch light onto an input waveguide at each of the plurality of wavelengths.

19. The system of claim 18, wherein the first detector is further configured to measure an output of the input waveguide and wherein the second detector is further configured to measure an output of an output waveguide that couples to the sensing ring.

20. A system for detecting a methane in an environment, comprising:
- a reference cell having a known concentration of methane gas;
- a ring resonator exposed to the environment;
- a first detector configured to measure a sensing signal at each of a plurality of wavelengths after each wavelength is coupled to the ring resonator, each said plurality of wavelengths being resonant in the ring resonator;
- a second detector configured to measure a reference signal at each of the plurality of wavelengths output by the reference cell; and
- a detection module configured to determine a set of wavelengths that correspond to an absorption curve of methane gas and to determine a concentration of methane in the environment by comparing amplitudes of the sensing signal at each of the set of wavelengths that correspond to the absorption curve to reference signals measured at each of the set of wavelengths.

* * * * *